United States Patent [19]

Hughes et al.

[11] Patent Number: 5,621,779
[45] Date of Patent: Apr. 15, 1997

[54] APPARATUS AND METHOD FOR DELIVERING RADIATION TO AN OBJECT AND FOR DISPLAYING DELIVERED RADIATION

[75] Inventors: John H. Hughes, Martinez; Francisco M. Hernandez, Concord; Aleksander Ustaszewski, Pleasant Hill; Randall V. Tarr, Concord, all of Calif.

[73] Assignee: Siemens Medical Systems, Inc., Iselin, N.J.

[21] Appl. No.: 504,722

[22] Filed: Jul. 20, 1995

[51] Int. Cl.⁶ .................................................. H05G 1/64
[52] U.S. Cl. .............................................. 378/65; 378/98
[58] Field of Search .................................. 378/145, 151, 378/97, 98, 96, 64, 65, 108

[56] References Cited

U.S. PATENT DOCUMENTS 3,783,251  1/1974  Pavkovich ................................. 378/65
5,148,032  9/1992  Hernandez ............................. 250/492.1

Primary Examiner—Don Wong

[57] ABSTRACT

Radiation output directed toward at least one field of an object, such as a patient, is sensed, for example, during a session of radiation therapy. The accumulated dose delivered to the field is displayed and updated throughout the delivery of radiation. A prescribed dose profile may also be displayed simultaneously so the user can compare the accumulated dose with the prescribed dose profile over the irradiated field. Dose profiles—both prescribed and accumulated—are preferably stored in a memory unit. Profiles for several different fields at several different times may be stored and used to direct and monitor the course of radiation treatment.

14 Claims, 3 Drawing Sheets

APPARATUS AND METHOD FOR DELIVERING RADIATION TO AN OBJECT AND FOR DISPLAYING DELIVERED RADIATION

BACKGROUND OF THE INVENTION

1. Technical Field

This invention relates to a radiation emitting device, and particularly to an apparatus and a method for displaying the radiation delivered to an object in a radiation treatment device.

2. Description of the Related Art

Radiation-emitting devices are generally known and used, for instance as radiation therapy devices for the treatment of patients. A radiation therapy device generally comprises a gantry which can be swiveled around a horizontal axis of rotation during the course of a therapeutic treatment. A linear accelerator is located in the gantry for generating a high-energy radiation (typically, of electrons or photons, that is, X-rays) beam for therapy. During treatment, this radiation beam is trained on one zone of a patient lying in the isocenter of the gantry rotation.

In order to control the radiation emitted toward an object, an aperture plate arrangement is usually provided in the trajectory of the radiation beam between the radiation source and the patient (or other object). This aperture plate arrangement defines a field on the patient to which a prescribed radiation is to be delivered. A wedge-shaped radiation distribution can be achieved by introducing, for example, a wedge-shaped absorption filter between the radiation source and the patient. Such devices, however, normally cannot display the actual emitted radiation delivered to the field; one common reason for this is that the system does not know the value of the wedge filter, that is, the amount by which it affects the emitted radiation, so that the systems cannot accurately predict delivered radiation.

U.S. Pat. No. 5,148,032 discloses a radiation therapy device in which isodose curves are adjusted both by a moveable plate that is controlled during irradiation and by varying the dose rate of the radiation beam during irradiation, so that a wide range of variation in the possible isodose curves is obtained. The delivery of radiation by such a radiation therapy device is prescribed and approved by an oncologist. Actual operation of the radiation equipment, however, is normally done by a therapist. When the therapist administers the actual delivery of the radiation treatment as prescribed by the oncologist, the device is programmed to deliver that specific treatment. For such a device it would also be very useful to display the delivered radiation so that the operator can be assured that the dose actually delivered correspond to the dose prescribed.

In light of the above, there is a need in the art for the visualization of the delivery of radiation to the object in order to verify that the radiation treatment device is doing what it is supposed to be doing.

SUMMARY OF THE INVENTION

According to the invention, a radiation source irradiates at least one field of an object, such as a patient, with an output beam. The beam is shielded to delimiting the output beam to the field. A radiation sensor, for example, a measuring chamber or a beam view device, senses radiation output delivered or directed toward the field via the shielded output beam and generates radiation output signals corresponding to radiation delivered to predetermined portions of the field. A processor then accumulates the radiation output signals and a display arrangement that displays the accumulated dose signals and for updates the display throughout the delivery of radiation.

The user may input to the processor a predetermined prescribed dose profile. The display arrangement then displays an indication of the prescribed dose profile simultaneously with the display of the accumulated dose signals. The display arrangement includes a display area that is at least a portion of a display screen, such as a window or icon; it may also include a printer.

In one embodiment, the beam is shielded using an arrangement that includes at least one movable plate positioned between the radiation source and the object. A plate position sensor is included for sensing the position of each movable plate. The display then displays the accumulated dose signals as a function of plate position.

In a preferred embodiment, a memory unit is connected to the processor for storing parameters of the predetermined prescribed dose profile and the accumulated dose signals.

In another embodiment, a fault-detection device is included for sensing malfunction, including system power loss, and for non-volatile storing in the memory unit of current accumulated dose signals upon sensing malfunction.

In yet another embodiment, a treatment verification and recording arrangement is included for downloading to the processing means profile parameters for a more than one sequential irradiation field of the object. The processor thereby stores in and retrieves from the memory unit accumulated dose signals for the plurality of irradiation fields.

DETAILED DESCRIPTION

The invention is described below with primary reference to a system for delivering X-ray radiation to a field of a patient, and for delimiting the field using at least one movable plate in the beam path from a radiation source. This is by way of example only. The invention may be used to display the delivery of any type of energy, for example, electrons (instead of X-rays), to any type of object (not just a human patient), provided the amount of energy delivered to the field can be sensed or estimated.

Furthermore, the invention may be used in, or in combination with, other technologies besides radiation therapy. For example, in computerized tomography (CT) scanning or imaging devices, the invention could be used in conjunction with a ring stack to indicate to the user how far along the CT scan has progressed.

Figure 1:
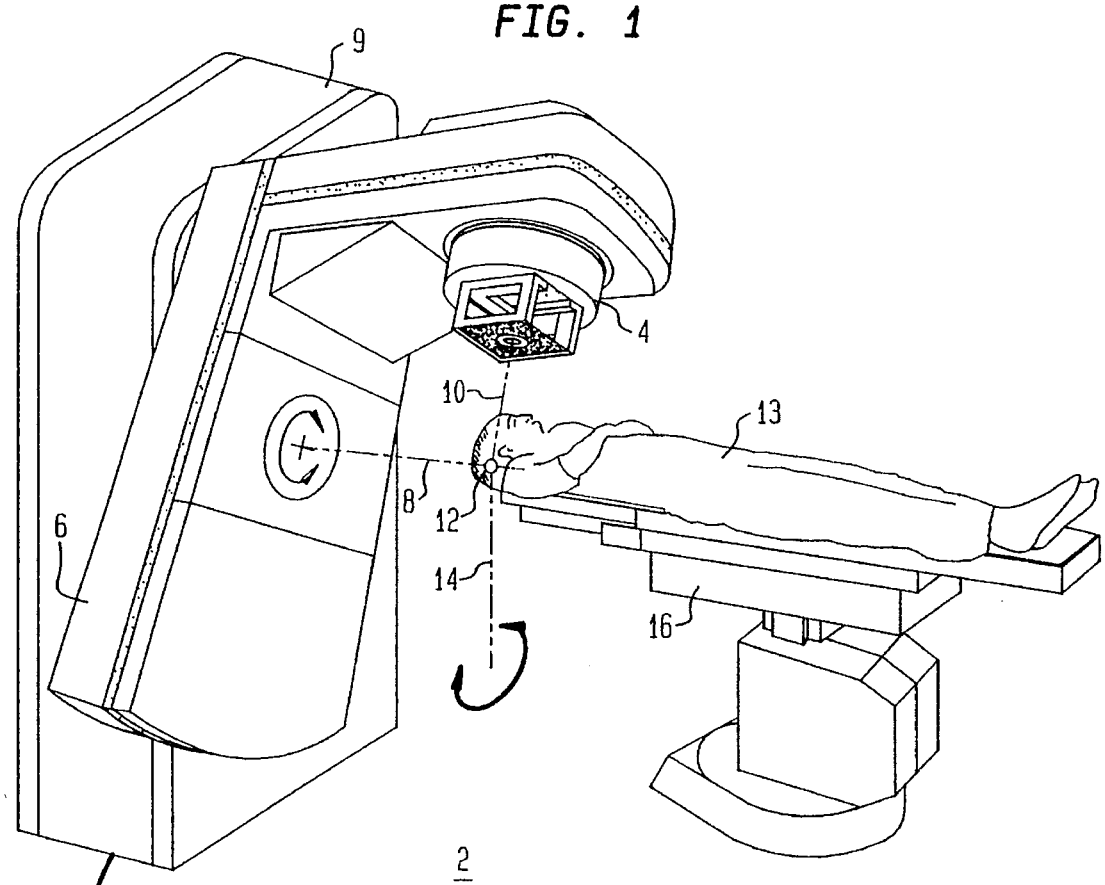
FIG. 1 shows a schematic diagram of a radiation treatment device including a treatment console constructed in accordance with the invention.
Figure 1:
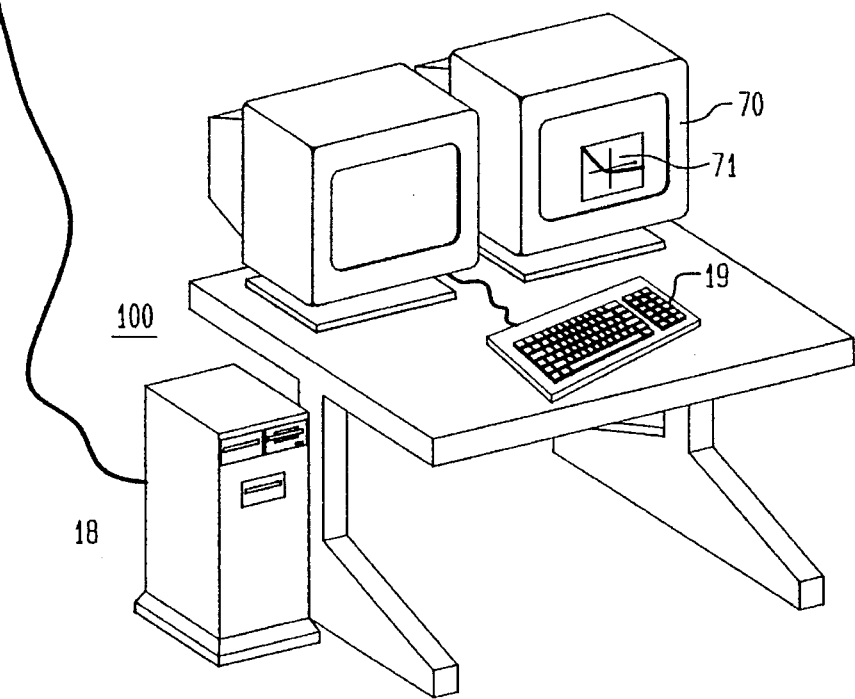

FIG. 1 shows a radiation treatment device 2 of common design, in which plates 4 and a control unit in a housing 9 and a treatment unit 100 constructed in accordance with the principles of the invention are used. The radiation treatment device 2 comprises a gantry 6 which can be swiveled around a horizontal axis of rotation 8 in the course of a therapeutic treatment. Plates 4 are fastened to a projection of gantry 6. To generate the high-powered radiation required for the therapy, a linear accelerator is located in gantry 6. The axis of the radiation bundle emitted from the linear accelerator and gantry 6 is designated by 10. Electron, photon, or any other detectable radiation can be used for the therapy.

During the treatment the radiation beam is trained on a zone 12 of an object 13, for example, a patient who is to be treated, and who lies at the isocenter of the gantry rotation. The rotational axis 8 of gantry 6, the rotational axis 14 of a treatment table 16, and the beam axis 10 all preferably intersect in the isocenter. The construction of such a radiation treatment device is described in general in a brochure "Digital Systems for Radiation Oncology", Siemens Medical Laboratories, Inc. A91004-M2630-B358-01-4A00, September 1991.

The area of the patient that is irradiated is known as the field. As is well known, the plates 4 are substantially impervious to the emitted radiation. They are mounted between the radiation source and the patient in order to delimit the field. Areas of the body, for example, healthy tissue, are therefore subjected to as little radiation as possible, and preferably to none at all. In the preferred embodiment of the invention, at least one of the plates is movable so that the distribution of radiation over the field need not be uniform (one region can be given a higher dose than another); furthermore the gantry can preferably be rotated so as to allow different beam angles and radiation distributions without having to move the patient around. Neither or these features is necessary according to the invention: the invention may also be used with fixed-field devices (no movable plates), with constant radiation delivery rates, and with fixed-angle beams (no rotatable gantry).

Moreover, plates, although common, are not the only type of beam-shielding devices that may be used. For example, in most radiation devices is some form of beam collimator, wedge, compensator, jaw, or other aperture device; the aperture device itself may in such cases act as the beam-shielding device, and the various beam-shielding devices may be combined to limit the field. The invention may be used with any such arrangement.

Radiation treatment device 2 also includes treatment unit 100 which is usually located apart from gantry 6 and treatment table 16. Preferably the radiation treatment device 2 is located in a different room to protect the therapist from radiation. The treatment unit 100 comprises an output device, such as a visual display unit or monitor 70, and a keyboard 19. Treatment unit 100 is routinely operated by the therapist who actually administers delivery of a radiation treatment as prescribed by an oncologist. The treatment unit includes a central processing unit (CPU) 18, whose function is described below. By utilizing keyboard 19, the therapist programs treatment unit 100 in a conventional manner to make sure that exactly the prescribed radiation is delivered to the patient. The program can also be input via another input device like a data storage device located within the central processing unit 18 or through data transmission to the CPU.

Various data can be displayed on the screen of monitor 70 before and during the treatment. Among these data the actual delivered radiation is visualized on the screen, particularly in a display area 71 which can cover the entire screen. Display area 71 can also cover only a portion of the screen and can be designed as a window or as an icon. In addition to the actual delivered radiation the prescribed radiation can also be shown on the screen. The display of the actual delivered radiation is preferably carried out in real time. Thus, at any time during treatment, the exact delivered radiation can be verified. In addition, at the end of the treatment, it is verified that the delivered radiation was exactly the same as the prescribed radiation. Instead of monitor 70, or in addition to it, other output devices, such as a printer can be provided.

Figure 2:
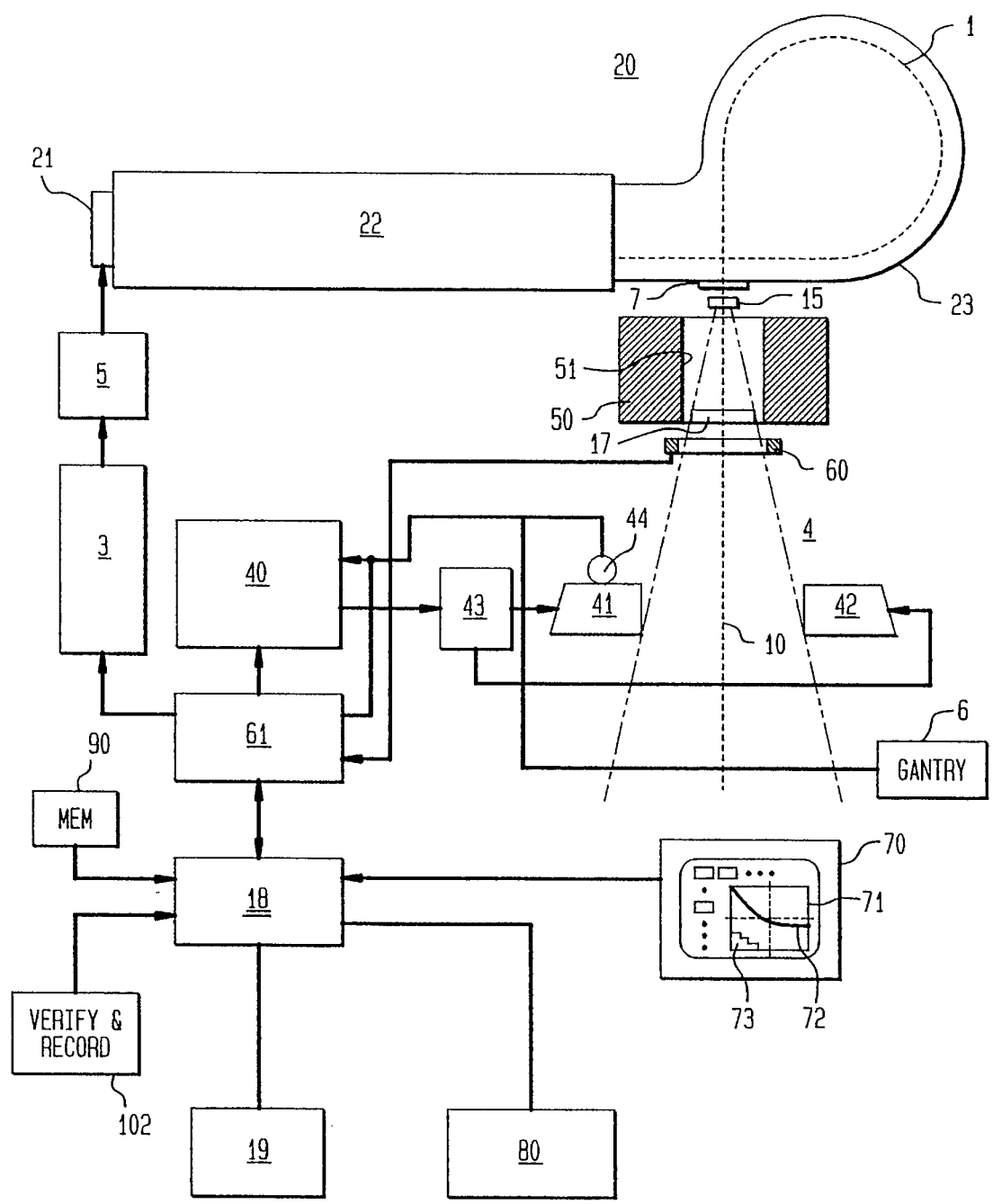
FIG. 2 is a block diagram illustrating portions of a processing unit, a control unit, and a beam generation system in the radiation treatment device of FIG. 1.

FIG. 2 shows portions of an illustrative radiation treatment device 2 and portions of treatment unit 100 in more detail. An electron beam 1 is generated in an electron accelerator 20. Accelerator 20 comprises an electron gun 21, a wave guide 22 and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, it is sent through a measuring chamber 60, in which the dose is ascertained. If the scattering foils are replaced by a target, the radiation beam is an X-ray beam. Finally, aperture plate arrangement 4 is provided in the path of radiation beam 1, by which the irradiated field of the subject of investigation is determined. Aperture plate arrangement 4 includes a pair of plates 41 and 42. As is described above, this is just one example of a beam-shielding arrangement that can be used in the invention. The invention will work with others also as long as there is an aperture plate arrangement that defines an irradiated field.

In the following, the invention is described in connection with a radiation treatment device in which at least one aperture plate is moveable during treatment. Such a device is described in U.S. Pat. No. 5,148,032. However, the invention can be carried out also with plates which are stationary during treatment. As described in this U.S. patent, in such a radiation treatment device, various wedge-shaped isodose curves can be easily achieved without a physical wedge being present in the trajectory of the beam.

Plate 41 is moved by a drive unit 43. Drive unit 43 comprises an electric motor which is coupled to plate 41 and which is controlled by a motor controller 40. A position sensor 44 is also coupled to plate 41 for sensing its position.

Motor controller 40 is coupled to a dose control unit which includes a dosimetry controller 61 for providing set values for the radiation beam energy in correlation with the position of plate 41 for achieving a given isodose curve. The amount or quantity of the radiation beam is measured, for example, by a measuring chamber 60. In response to the deviation between the set values and the actual values, dosimetry controller 61 supplies signals to trigger system 3 which change the pulse repetition frequency so that the deviation between the set values and the actual values of the radiation beam is minimized. Thus, the dose control unit controls the dose rate of the radiation beam in correlation with the movement of plate 41 in order to achieve the given isodose curve. The ability to change the dose rate is generally known and it can be changed for instance by a digital dosimetry system.

The invention may operate using any form of sensor or arrangement that determines the radiation output that is directed at the field. In the illustrated embodiment of the invention the amount or quantity of the radiation beam is measured, for example, by a conventional measuring or dose chamber 60. This is not necessary. Instead, for example, a portal imaging or beam view device may be included so that radiation is sensed after it has passed through the patient. In such case, conventional calibration techniques are applied to compensate for sensed output deviations that are caused by absorption or scattering by the patient. Furthermore, it is not necessary according to the invention to measure the absolute value of the dose; instead, sensing devices may be used that measure the dose rate, which may then be integrated by either hardware or software to provide a value of the actual dose, which is then displayed in the manner described below.

FIG. 2 also shows various portions of treatment unit 100. Monitor 70 and keyboard 19 are connected to the central processing unit 18. A printer 80 can also be provided to record the protocol of the treatment. Central processing unit 18 is programmed to control radiation treatment device 2 and to carry out the method according to the invention. According to the instructions of the oncologist, the therapist programs central processing unit 18 in any known manner so that it carries out the prescribed course (or series of courses of) of radiation treatment. In window 71 on the screen of monitor 70, curve 72 indicates the prescribed delivery of the radiation treatment.

The horizontal axis of display area 71 shows the movement of moveable plate 41 from its initial position to its final position during treatment. The horizontal axis may be graduated in any convenient manner; for example, with respect to the middle of the opening created by the movement the initial position may be marked as −0.5 or −50% of the opening size, and the final position may be marked +0.5 or +50% of the opening size. The vertical axis indicates, for example, by means of a line, by shading or by coloring, the prescribed accumulated dose during treatment, starting from a preset value, measured for example, in MU (Monitor Units), and also an indication of the actual accumulated dose during treatment. The unit MU is a unit of radiation from which the absorbed dose can be calculated; one MU is normally calibrated to 1 cGy. Curve 72 indicates the prescribed accumulated dose of radiation versus the position of moveable plate 41 and diagram 73 monitors the total actually delivered accumulated dose.

The prescribed dose curve 72 is generated by the monitor in any conventional manner to correspond to the dose profile entered by the user via the input device (keyboard, downloaded data, etc.). Note that the window 71 contains a discretized representation of the position and irradiation of the field—the plate position (which define the "edge" of a region of the field) is represented as small position intervals (x-axis) and delivered dose is represented as small dose intervals (y-axis). (In this illustration, only one plate is moved, but, as is explained below, multiple-dimension displays are also possible, for example, when more than one plate is moved.) As is explained above, the quantity or rate of the dose is sensed and measured by some known device such as the measuring or dose chamber 60, or a beam view device beneath the patient. Signals corresponding to the dose are passed to the dosimetry controller 61, which in turn applies dosimetry signals to the CPU 18. The CPU 18 then generates, in a known manner, corresponding signals to conventional display drive circuitry in the monitor 70.

Diagram 73 is for example a beam-like diagram resembling a "growing bar chart" that shows the accumulated dosage in columns in increments of for instance 5% or finer of the total accumulated dosage. As the accumulated dose for a given plate position (which also determines which portions of the field are irradiated) increases, the respective "bars" are made taller. If the area under curve 72 is marked in a first color different from a background color and beam-like diagram 73 has a second color, than the operator will easily be able to see how the treatment progresses and how the accumulated MU is distributed in the field irradiated by the beam. Display area 71 thus changes its content as the treatment progresses and it can be verified that the dose provided to object 13 does not exceed the prescribed dose.

It is also possible to set an alarm, or to shut off radiation treatment device 2, if diagram 73 exceeds curve 72 by a certain threshold. In this case, the CPU compares the accumulated dose for each plate position with the prescribed dose, and if the accumulated dose (or some function of it) exceeds the prescribed dose by a pre-set threshold amount, then the CPU can direct the monitor to give off an alarm sound, cause some part of the display to flash or change color, for example, turn red, or give some similar warning, and it can also direct the dosimetry controller 61 to halt irradiation.

For the calculation of the accumulated dosage in display area 71 the following data may be used by a processor included in central processing unit 18:

MUprev=MU from last update

MUcurrent=latest reported MU from dosimetry controller 61

Pplate=latest reported position of plate 41

MUcol[i]=array of cumulative dose at midpoint of each beam-like column.

During initialization, MUprev and MUcol[i] are set to 0, and for the update processing for each column corresponding to an increment on the x-axis the following steps are carried out:

Sense position of plate 41

If position of plate 41 is beyond the midpoint of the column,

Add(MUcurrent−MUprev) to MUcol[i]

Display column MUcol[i].

Central processing unit 18 is connected to dosimetry controller 61 for transferring the desired values of radiation, dependent on the position of moving plate 41 as the desired values are shown in display area 71. Dosimetry controller 61 then supplies signals to trigger system 3, which changes the pulse repetition frequency in a corresponding manner. Motor controller 40 controls drive unit 43 to perform the desired movement of plate 41. The output signals of position sensor 44 are conveyed to central processing unit 18 for calculating the momentary value of the horizontal axis. The output signals of measuring chamber 17 are transmitted to central processing unit 18 for calculating the accumulated dose for display in diagram 72 in the vertical axis of display area 71.

Accumulated dose values, and preferably also the values and other parameters of the prescribed dose and field geometry, are preferably stored in a memory unit 90. The memory unit 90 is connected to or contained within the CPU 18.

If, in a second pair of plates 4, at least one other plate is moved, or if gantry 6 is moved during treatment, the radiation is displayed correspondingly, for instance by utilizing a third axis for a three dimensional display or by using polar coordinates.

Alternatively, the field may be represented in two dimensions on the display screen so that it appears with the actual geometry of the field. For example, a wedge-shaped or arcuate sector field could be displayed in a conventional manner as a pattern of picture elements ("pixels") with a predetermined resolution. Rather than having a "growing bar chart," the color of each pixel could, for example, change from black or blue and, as the dose at each corresponding point increases, its color could be displayed as increasingly green, then yellow, then red. Yellow could, for example, indicate that the prescribed dose has been reached, and red could be used to show a dose above that prescribed. Accumulated dose could also be displayed in a "topographic" format, with dose contour lines displayed connecting pixels with at least approximately the same accumulated dose. The contour lines would of course change during treatment, and the display may also be color-coded as in the previously mentioned example.

It is also possible according to the invention to sense and display in "real-time" (that is, continuously changing during actual administration of the radiation treatment) accumulated dosage data corresponding to one or more 3-D fields, which, for example, may represent the volume of a tumor. Depth information may then be derived in any conventional manner from the geometry of the radiation-emitting device, such as the position of the gantry. The system will then store accumulated dose data in a 3-D table in the memory 90. Using conventional display methods, the monitor 70 then displays selected cross-sectional views of accumulated dose; conventional methods may be used to enable the user to select, via the input device, which cross-section is to be viewed and "tracked" at any one time. Alternatively, more than one display window 71 may be displayed on the display screen of the monitor at any one time, with each window showing the progress of dose accumulation in different cross-sectional planes of the 3-D field. Note that this technique is particularly suitable for use in combination with other technologies such as CT, which display images as planar views from different depths.

In order to improve accuracy and registration (for example, to compile accumulated 3-D dosage data for display), the CPU 18 may also be connected to conventional circuitry that indicates the position and orientation of the table or other surface on which the patient lies during treatment. This data may be used instead of or in conjunction with gantry position data to provide information about the position of any portion of the field.

Figure 3A:
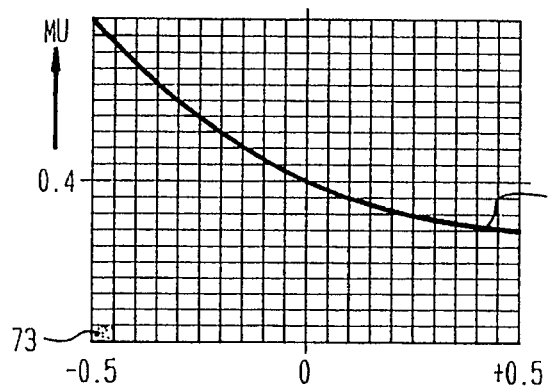
FIGS. 3a to 3c show graphs of a planned delivery of radiation and the actually delivered radiation for a wedge-shaped dose distribution at various points of time.
Figure 3B:
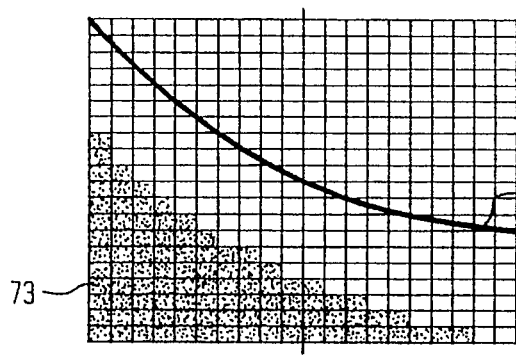
Figure 3C:
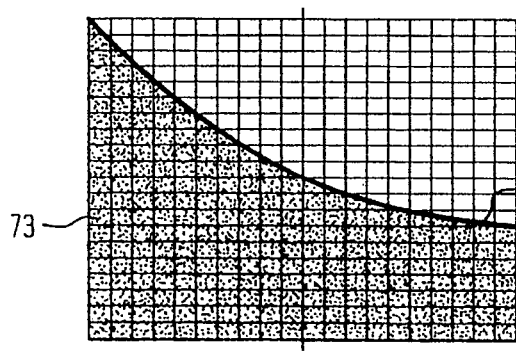

FIGS. 3a to 3c show an example of the visual representation of the accumulated dose in the display area 71 during treatment at three different stages. In FIG. 3a the treatment has just begun and plate 41 has only moved slightly. In FIG. 3b about half of the accumulated dosage has been delivered, and in FIG. 3c the treatment is finished.

Figure 4A:
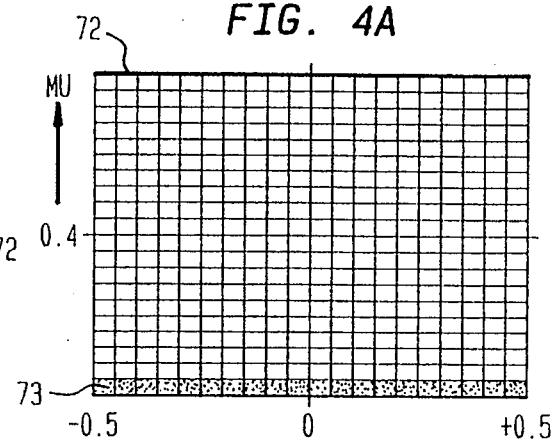
FIGS. 4a to 4c show graphs of a planned delivery of radiation and the actually delivered radiation for an equal dose distribution at various points of time.
Figure 4B:
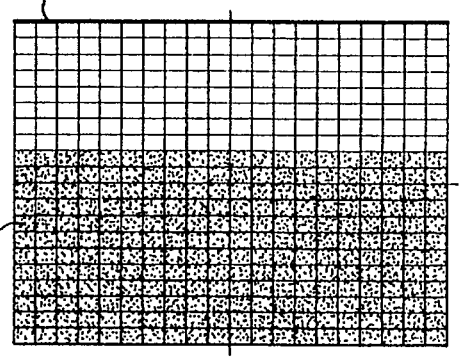
Figure 4C:
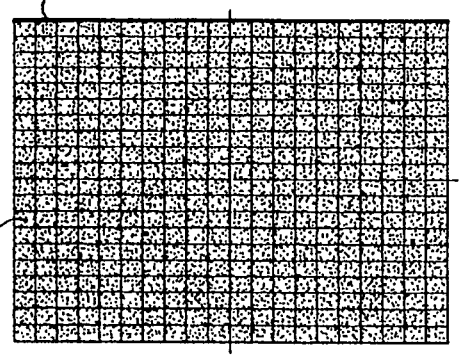

FIGS. 4a to 4c show an application of the invention in a radiation treatment device in which plates 41 and 42 are stationary. Monitor 70 then shows for example a diagram which, as treatment progresses, fills up the area provided in display area 71 from the bottom to the top by beams extending over the entire width of display area 71.

Display area 71 can cover the entire screen or only a portion of it, in which case it can be displayed as a window or as an icon. As is mentioned above, the field does not have to be represented as a rectangular area; rather, it can also show annular or sector dose regions in arbitrary geometry, as long as the dose is sensed as a function of the irradiated field. Furthermore, the dose can also be displayed by using three dimensional diagrams which are generated in a conventional manner by using a third axis. Such three dimensional displays are particularly advantageous if more than one plate and/or the gantry 6 are moved during irradiation.

The memory unit 90 is preferably non-volatile. Furthermore, the CPU 18 preferably also includes or is connected to conventional failure or fault-detection and power sensing circuitry that indicates any malfunction of the system or any drop below full, proper operating power of the system. Power drops need not be total; partial power loss ("brownouts") might also occur. When such a condition is sensed, the CPU ensures that the most recent accumulated dosage data, the parameters defining the geometry of the field, and preferably even date and time information, are stored in the memory unit. Note that as long as the CPU continuously updates the accumulated dose values stored in the memory unit, and the memory is non-volatile, this will happen "automatically." In this way, when power is restored, treatment will be able to resume quickly from where it was halted, without uncertainty about the accumulated dose.

One other advantage of non-volatile memory is that it makes it easy and accurate to administer a course of treatment during more than one session. In this case, the data for each field of each patient is stored in a conventional data base (and may, for the sake of redundancy and security, be loaded onto a secondary back-up storage medium such as a disk) and can be called up as each partial phase of a full course of treatment is begun.

It has been assumed above by way of example that the dose profile to be followed for each field is input by the operator. This is not necessary. Assume, for example, that, after one treatment session, the actually delivered accumulated dose profile (which the user will see displayed) is particularly advantageous or successful, perhaps even better than the originally prescribed profile. The final values of the previous accumulated dose curve (or, in the multi-dimensional case, surface) will have been stored in the memory unit. These final values may instead be used and displayed as the "prescribed" dose profile for the following treatment.

By connecting an external device (such as another, possibly even remote processor or physician's workstation) to the memory unit, preferably via the CPU 18, treatment parameters (field geometry, dosage profile, patient identification data, etc.) can be downloaded directly into the memory unit 90. This data is then accessible by the CPU so that it can direct the course of the treatment and display accumulated dose as described above.

A "course" of radiation treatment may, and often does, have more than one field, and may run over several different sessions. In some cases, hundreds of different (and, in some cases, fixed) sequential fields are used during a course, for example, to provide proper irradiation of a field that has a complicated geometry or prescribed dose profile, to lessen discomfort to the patient, or to adjust the field as a tumor shrinks during treatment. The invention therefore also comprises an optional verification and recording system 102 (see FIG. 2), which stores and downloads to the radiation system (via the CPU 18 or directly into the memory 90) the parameters for the various fields of the course of treatment. Note that this may include the accumulated dose values for each field obtained from the earlier treatment sessions. In order to provide a permanent record of the course of treatment, the accumulated dose values for different fields, possibly also at different times, may be printed out on the printer 80.

We claim:

1. A system for delivering and displaying radiation delivered to an object, the system comprising:

a radiation source with an output beam;

beam-shielding means for delimiting the output beam to at least one predetermined irradiation field of the object;

sensing means for sensing radiation output of the shielded output beam and for generating radiation output signals corresponding to radiation output delivered to predetermined portions of the field;

processing means for accumulating the radiation output signals; and display means for displaying the accumulated dose signals and for updating the display throughout the delivery of radiation;

input means for inputting to the processing means a predetermined prescribed dose profile, wherein the display means is further provided for displaying an indication of the prescribed dose profile simultaneously with the display of the accumulated dose signals.

2. A system for delivering and displaying radiation delivered to an object, the system comprising:

a radiation source with an output beam;

beam-shielding means including at least one movable plate positioned between the radiation source and the object for delimiting the output beam to at least one predetermined irradiation field of the object;

a plate position sensor for sensing the position of at least one plate of a plate arrangement;

sensing means for sensing radiation output delivered to the field via the shielded output beam and for generating radiation output signals corresponding to radiation delivered to predetermined portions of the field;

processing means for accumulating the radiation output signals; and display means for displaying the accumulated dose signals as a function of plate position on at least a portion of a display screen and for updating the display throughout the delivery of radiation;

input means for inputting to the processing means a predetermined prescribed dose profile, wherein the display means is further provided for displaying an indication of the prescribed dose profile simultaneously with the display of the accumulated dose signals; and a memory unit that is connected to the processing means for storing parameters of the predetermined prescribed dose profile and the accumulated dose signals.

3. A system as in claim 1, wherein the display means includes a display area that is at least a portion of a display screen.

4. A system as in claim 1, wherein the display means includes a printer.

5. A system as in claim 1, in which:

the beam-shielding means includes at least one movable plate positioned between the radiation source and the object;

a plate position sensor is provided for sensing the position of at least one movable plate of a plate arrangement;

the display means displays the accumulated dose signals as a function of plate position.

6. A system as in claim 1, in which the sensing means includes a measuring chamber located between the radiation source and the object.

7. A system as in claim 1, further including a memory unit that is connected to the processing means for storing parameters of a predetermined prescribed dose profile and the accumulated dose signals.

8. A system as in claim 7, further including:

fault-detection means for sensing malfunction, including system power loss, and for non-volatile storing in the memory unit of current accumulated dose signals upon sensing malfunction.

9. A system as in claim 7, further including:

treatment verification and recording means for downloading to the processing means profile parameters for a plurality of sequential irradiation fields of the object;

the processing means being further provided for storing in and retrieving from the memory unit accumulated dose signals for the plurality of irradiation fields.

10. A method for delivering and displaying radiation delivered to an object, comprising the following steps:

selecting at least one irradiation field of the object;

generating an output beam of radiation from a radiation source;

shielding the beam and thereby delimiting the output beam to irradiating each field;

sensing radiation output directed towards the field from the radiation source;

generating radiation output signals corresponding to radiation delivered to predetermined portions of the field;

accumulating the radiation output signals;

displaying the accumulated dose signals and updating the display throughout the delivery of radiation;

inputting to the processing means a predetermined prescribed dose profile; and displaying an indication of the prescribed dose profile simultaneously with the display of the accumulated dose signals.

11. A method as in claim 10, in which the step of shielding includes moving at least one movable plate positioned between the radiation source and the object, further including the following steps:

sensing the position of each movable plate; and displaying the accumulated dose signals as a function of plate position.

12. A method as in claim 10, further including the step of storing in memory unit parameters of a predetermined prescribed dose profile and the accumulated dose signals.

13. A method as in claim 12, further including the following steps:

sensing malfunction, including system power loss; and non-volatile storing in the memory unit of current accumulated dose signals upon sensing malfunction.

14. A method as in claim 12, further including the following steps:

downloading to the memory unit profile parameters for a plurality of sequential irradiation fields of the object; and storing in and retrieving from the memory unit accumulated dose signals for the plurality of irradiation fields.

* * * * *